(12) United States Patent
Ireri (10) Patent No.: US 10,946,716 B2
(45) Date of Patent: Mar. 16, 2021

(54) VEHICLE TEMPERATURE SENSOR SYSTEMS

(71) Applicant: Eric Ireri, Poway, CA (US)

(72) Inventor: Eric Ireri, Poway, CA (US)

(*) Notice: Subject to any disclaimer, the term of this patent is extended or adjusted under 35 U.S.C. 154(b) by 243 days.

(21) Appl. No.: 15/437,937

(22) Filed: Feb. 21, 2017

(65) Prior Publication Data

US 2017/0240022 A1 Aug. 24, 2017

Related U.S. Application Data

(60) Provisional application No. 62/297,885, filed on Feb. 21, 2016.

(51) Int. Cl.
| | | |
|---|---|---|
| *B60H 1/00* | (2006.01) | |
| *B60J 1/12* | (2006.01) | |
| *B60N 2/00* | (2006.01) | |
| *B60R 21/015* | (2006.01) | |
| *B60N 2/26* | (2006.01) | |
| *G08B 25/08* | (2006.01) | |
| *G08B 21/22* | (2006.01) | |
| *G08B 13/19* | (2006.01) | |

(52) U.S. Cl.
CPC ..... *B60H 1/00742* (2013.01); *B60H 1/00778* (2013.01); *B60N 2/002* (2013.01); *B60N 2/26* (2013.01); *G08B 13/19* (2013.01); *G08B 21/22* (2013.01); *G08B 25/08* (2013.01)

(58) Field of Classification Search
CPC .... B60H 1/00742; G08B 25/08; G08B 21/22; G08B 13/19; B60N 2/26; B60N 2/002
See application file for complete search history.

(56) References Cited

U.S. PATENT DOCUMENTS

| 7,348,880 B2 | 3/2008 | Hules |
|---|---|---|
| 7,710,277 B2 | 5/2010 | Wilson |
| 8,836,491 B2 | 9/2014 | Rao |

(Continued)

FOREIGN PATENT DOCUMENTS

| CN | 202573985 | 5/2012 |
|---|---|---|
| CN | 104325946 | 2/2015 |

(Continued)

*Primary Examiner* — Hunter B Lonsberry
*Assistant Examiner* — Mathew Franklin Gordon
(74) *Attorney, Agent, or Firm* — Varnum LLP (57) ABSTRACT

A vehicle having a system which includes at least one sensor contained therein. The systems utilizes conditional probability to determine if an occupant (i.e. child and/or animal) is in the vehicle in the absence of an adult. The system used conditional probability to predict the likelihood that a child and/or animal was left unsupervised within the vehicle. The system collects data from existing vehicle sensors (door sensor, weight sensor, seatbelt sensor, face detection sensor, input sensors or any other suitable sensor already imbedded within the hardware of the vehicle) and uses that data to assume if an adult, child and/or animal is present. A motion sensor and a temperature sensor (infrared camera) are further utilized to determine the presence of a child/animal and the temperature of a child. Input from the motion sensor and/or temperature sensor (infrared camera) are utilized to provide warnings or to take corrective measures.

17 Claims, 5 Drawing Sheets

(56) References Cited

U.S. PATENT DOCUMENTS

| | | | | |
|---|---|---|---|---|
| 8,970,381 | B2* | 3/2015 | Heath | A61B 5/1171 |
| | | | | 340/573.1 |
| 9,000,907 | B1* | 4/2015 | Rembach | B60N 2/002 |
| | | | | 340/457 |
| 9,517,679 | B2 | 12/2016 | Frank | |
| 2007/0243854 | A1* | 10/2007 | Taki | G08B 21/06 |
| | | | | 455/404.1 |
| 2009/0040036 | A1* | 2/2009 | Talis | B60N 2/002 |
| | | | | 340/457.1 |
| 2015/0075763 | A1 | 3/2015 | Kim | |
| 2016/0082808 | A1* | 3/2016 | Perkins | B60H 1/00871 |
| | | | | 165/11.2 |
| 2016/0171859 | A1* | 6/2016 | Bowlus | G08B 21/02 |
| | | | | 340/457 |
| 2016/0272114 | A1 | 9/2016 | Medina | |

FOREIGN PATENT DOCUMENTS

| | | |
|---|---|---|
| CN | 105046878 | 11/2015 |
| CN | 105205982 | 12/2015 |
| WO | WO2016149746 | 9/2016 |

\* cited by examiner

VEHICLE TEMPERATURE SENSOR SYSTEMS

CROSS-REFERENCE TO RELATED APPLICATIONS

This application claims priority of U.S. Provisional Patent Application Ser. No. 62/297,885 filed Feb. 21, 2016, which is incorporated herein by reference.

TECHNICAL FIELD

The present specification generally relates to a sensor system and, more specifically, a sensor system for a vehicle for detecting presence and/or health of humans and/or animals within the vehicle.

BACKGROUND

There have been 637 infant deaths by heatstroke in automobiles since 1998. This tragedy prompted the National Highway Traffic Safety Administration (NHTSA) to perform a study that tested the effectiveness of available commercial solutions to prevent heatstroke. It concluded that all existing devices require too much user input, and are inconsistent in their results resulting in false positives or failed operation.

Furthermore, determining if a child is sick is frequently not determined until well after the child has been running a fever for a length of time. If it is determined if a child is running a fever, measures can be taken to reduce fever, reduce symptoms and make the child more comfortable.

Accordingly, a need exists for alternative means for determine if a child and/or animal is contained within the vehicle and adjusting vehicle settings to compensate for the presence of a child and/or animal.

SUMMARY

In one embodiment, a vehicle occupant temperature sensing system may include at least one existing sensor within a vehicle, a motion sensor provided within an interior of the vehicle, a processor configured to determine if a child, adult and/or animal is contained within the vehicle, the processor configured to determine the presence of a child, adult and/or animal based on data receive from both the at least one existing sensor and the motion sensor and a temperature sensor (also referred to as an infrared camera) configured to take the temperature of a child and/or animal if it is determined, based on data from both the at least one existing sensor and the motion sensor, that a child and/or animal is contained within the vehicle. The vehicle occupant temperature sensing system may further provide where the at least one existing sensor is a seatbelt sensor wherein a signal is sent to the processor indicating if the seatbelt is fastened or unfastened. In other embodiments, the at least one existing sensor is a weigh sensor wherein a predetermined weights threshold determines if a child, adult and/or animal is contained within the vehicle. Alternatively or in addition to, the at least one existing sensor is a door sensor wherein a signal is sent to the processor if it determines that a driver has left the vehicle, but the passengers may not have left the vehicle. The at least one existing sensor may also be a facial recognition (for known occupants) or eye or eye movement recognition (for unfamiliar occupants) sensors.

In some embodiments, the processor is configured to control corrective actions of the vehicle if it is determined that the temperate of the child and/or animal is elevated. In some embodiments, the corrective action include turning on the air conditioning. In other embodiments, a display message is conveyed to the user of the vehicle if an elevated temperature is detected. A display message may also be conveyed to the user if the elevated temperature may be associated with an illness.

In another embodiment, a vehicle occupant temperature detection system may include at least one existing vehicle sensor, a temperature sensor configured to acquire a body temperature of a vehicle occupant, the temperature sensor configured to activate upon a signal from the at least one existing vehicle sensor that an occupant is in the vehicle and a processor in communication with the temperature sensor, the processor configured to determine if the body temperature of the occupant is above or below a predetermined threshold wherein if the body temperature of the occupant is above the predetermined threshold, then the processor is configured to notify the user of the elevated temperature and/or configured to take corrective measures to reduce the body temperature of the occupant. The vehicle occupant temperature sensing system may further provide where the at least one existing sensor is a seatbelt sensor wherein a signal is sent to the processor indicating if the seatbelt is fastened or unfastened. In other embodiments, the at least one existing sensor is a weigh sensor wherein a predetermined weights threshold determines if a child, adult and/or animal is contained within the vehicle. Alternatively or in addition to, the at least one existing sensor is a door sensor wherein a signal is sent to the processor if it determines that a driver has left the vehicle, but the passengers may not have left the vehicle. The at least one existing sensor may also be a facial recognition sensor.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

FIG. 1-7 generally depict a vehicle having a system which includes at least one sensor, or a plurality of sensors, contained therein. The systems utilizes conditional probability to determine if an occupant (i.e. a child and/or an animal) is in the vehicle in the absence of an adult. The system uses conditional probability to predict the likelihood that a child and/or animal was left unsupervised within the vehicle. The system collects data from existing vehicle sensors (door sensor, weight sensor, seatbelt sensor, face detection sensor, input sensors or any other suitable sensor already imbedded within the hardware of the vehicle) and uses that data to assume if an adult, child and/or animal is present. Based on this determination, a motion sensing or temperature sensing process may begin to initiate. If it is determined that a temperature is elevated, corrective and/or notification actions may occur.

In the present embodiment, the temperature detection sensor is an infrared camera. In this embodiment, the sensor is a digital infrared camera configured to take an image of an occupant. From that image, the processor can 1) verify if the object is a child and/or animal and 2) determine the temperature of the child. The infrared photo will determine, based on the elements in the array, the temperature of the child in the car seat. It is noted that the temperature sensor may be any camera or other sensor configured to 1) verify if the object is a child and/or animal and 2) determine the temperature of the child. In this specification, the terms camera and sensor may be used interchangeable when referring to determining and detecting the temperature of a child occupant.

A movement or motion sensor is also provided within the vehicle. The motion sensor may be independent of the temperature sensor, as described above. The primary purpose of the motion sensor is to prevent heatstroke (and chocking) within a vehicle. If, based on input received from existing sensors within the vehicle, the motion sensor determines that there is a child and/or animal within the vehicle and the ambient temperature is above a predetermined threshold, then the processor will notify the owner of the vehicle and/or take corrective and preventative measures (i.e. turn on the air conditioning). Specific examples of these embodiments will be discussed in the following.

The sensor of the present specification is configured to monitor movement and/or body temperature of a human and/or animal contained within the vehicle. This sensor is in addition to the existing vehicle sensors used to determine the conditional probability that an adult, child and/or animal is present. The system is configured to use existing sensors already contained within standard vehicles to determine if a temperature of a child and/or animal should be monitored. The sensors are connected to a (CPU or equivalent) processor which is configured to process and adjust vehicle settings (and/or send alerts) to make the human and/or animal contained within the vehicle more comfortable.

The sensor system may be referred to as a Smart Infrared Thermography Infant Malady Detector and Heatstroke Preventer (SMIRT). The system or SMIRT is the first of its kind, integration of medical technology with an automobile. It is designed to detect human temperature through the use of infrared thermography (also referred to as IRT). SMIRT is designed, but not limited to taking accurate temperature readings that can be processed to detect infections and maladies that have in part, high fever as a symptom. It takes advantage of a modern car's connected systems and existing sensors to alert a parent, or care giver of the child passenger's condition through the vehicles warning systems.

In some embodiments, the system is configured to convey illness directly to a doctor or other health professional. In this embodiment, a message is sent to a predetermined doctor or health professional. The system may automatically set up an appointment or prompt a user to schedule a processional. In other embodiments, the system merely conveys the elevated temperature to the doctor or other health professional for record keeping purposes.

Temperature sensing, specifically infrared camera image processing such as used in the present specification, is accomplished safely, wirelessly, and requires no human intervention, or physical attachment to a car seat to ensure reliable operation. The system design has the added benefit of preventing infant heatstroke related fatalities that have hereto lacked a concrete engineering solution, by alerting parent/caregiver, and or turning on the cars and its air-conditioning system on.

The system acquires accurate temperature readings notwithstanding ambient temperature conditions. The system utilizes an infrared camera to distinguish the temperature of an occupant as compared to the temperature of the surrounding objects (seats, pillars . . . etc.) and the ambient temperature. The infrared camera is configured to view the radiation from the occupant and not from the surrounding inanimate objects. In this specification, the terms temperature sensor and infrared camera (or any variations thereof) may be used interchangeably are designed to designate the camera or sensor configured to determine a bodily temperature of a child and/or animal using infrared technology or infrared thermography, also known as ITR.

The system is configured to discern the difference between an adult and a child passenger. Furthermore, the system further identifies the presence of a child even when covered by a blanket of obscured by a car seat. In this embodiment, a motion sensor is utilized to detect minor movements of the occupant's chest cavity. Data measured from movement of an occupant's chest cavity may dictate whether the occupant is an adult, child or animal. If the chest cavity (distance travelled) movement is minimal with, the processor assumes that the occupant is a child or animal. If the chest cavity distance travelled is higher than that of a pre-determined distance, then it is assumed to be a child. After its been determined by the processor that the occupant is a child, choking can be determined because normal breathing will have a constant velocity, while choking velocity will be intermittent. Distance traveled is greater in adults, the processor then assumes that the occupant is an adult. Using this system, movement of the chest cavity may be detected even with the occupant is covered by a blanket or other cover.

In some embodiments, the motion sensor (or movement sensor) is a radar movement sensor. As stated above, this sensor is configured to detect chest movement including both the distance traveled and velocity of travel. This system also allows checking of whether or not an occupant is breathing, or can determine if the occupant is choking.

The system is automated, requires no human intervention to ensure safe and reliable operation. The system does not require a prompt from the users of the vehicle to initiate the process. In this, the system is autonomous. No parent/caregiver intervention or action will be required to ensure smooth operation.

The system is designed for, but not limited to integration into a vehicle in the manufacturing process. The system may be integrated directly into the vehicle at manufacturing, or it may be provided as an aftermarket option.

The system connects to a Media Oriented Systems Transport (MOST), or Controller Area Network (CAN) bus. The MOST or CAN may be used as the processor. Other similar processors or controllers may also be used within the system.

The system also has the capability to automatically adjust temperature settings within a vehicle based on the temperature of an occupant. Young children and animals do not have the ability to properly articulate that they are uncomfortable, particularly hot or cold. Accordingly, the present system may be used to automatically detect the temperature of an occupant and adjust the temperature settings in an effort to control the body temperature of an otherwise healthy occupant (animal, child and/or animal). This embodiment may also be features as a smart system and promoted as a luxury feature within the system. This system may be utilized and focused on particular zones within the vehicle.

Figure 1:
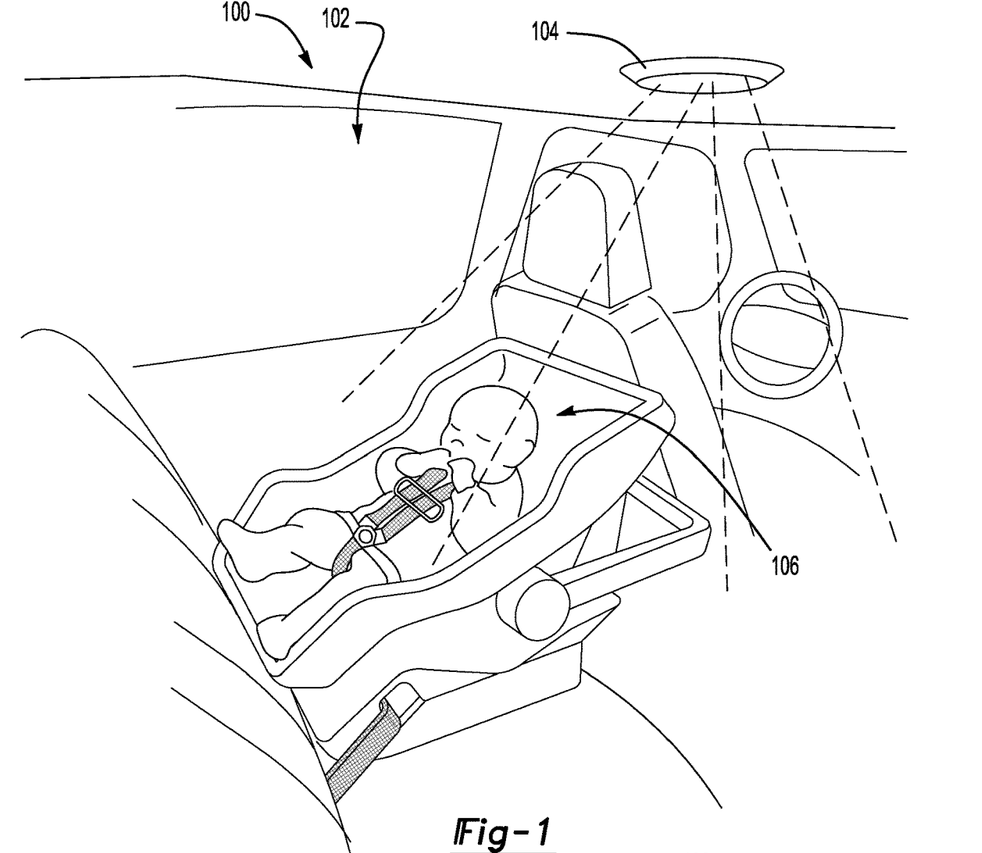
FIG. 1 depicts a perspective environmental view of a sensor of the present specification with a child in a car seat according to one or more embodiments shown and described herein.
Figure 2:
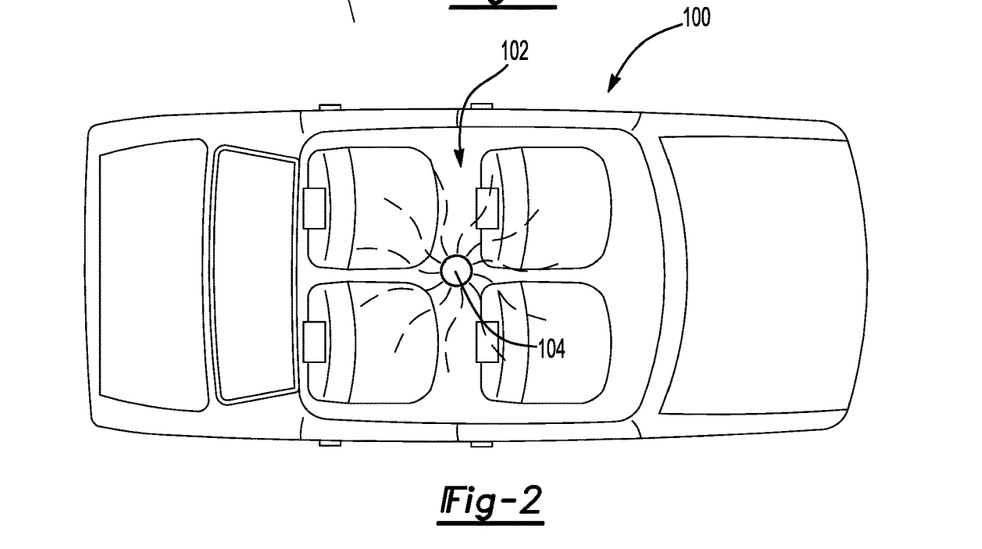
FIG. 2 depicts a top view of a vehicle having a plurality of the present specification with a child in a car seat according to one or more embodiments shown and described herein.

Generally, a vehicle 100 of the present specification includes a vehicle interior 102. A sensor (temperature and/or motion) 104 is provided in a position advantageous to "view" all occupants within the vehicle. In the embodiment as illustrated in FIG. 1, the sensor 104 is provided on the roof of the vehicle 100 in the interior 102. In other embodiments, the sensor 102 is provided on the rear view mirrors, on the roof at a more forward location, on the dashboard . . . etc.

Figure 4:
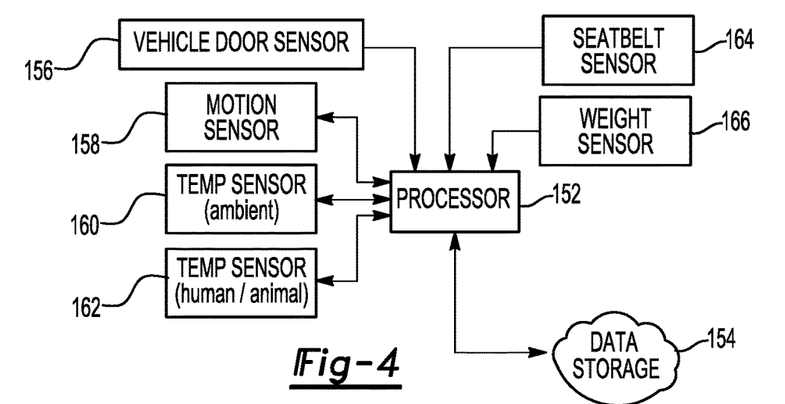
FIG. 4 depicts a system having a plurality of sensors according to one or more embodiments shown and described herein.

As illustrated by FIG. 4, the system generally includes a processor 152. The processor is in direct communication with a plurality of existing sensors within the vehicle 100. The following are examples of existing sensors in communication with the processor 152: a vehicle door sensor 156, a seatbelt sensor 164 and a weight sensor 166. Other existing sensors or future sensors may also be used such as herein disclosed. The processor 152 is also in communication with a motion sensor 158, a temperature sensor 160 (to detect ambient temperature) and a temperature sensor 162, specifically an infrared camera, (to detect occupant temperatures). The temperature sensor 162 is an infrared temperature camera.

Figure 3:
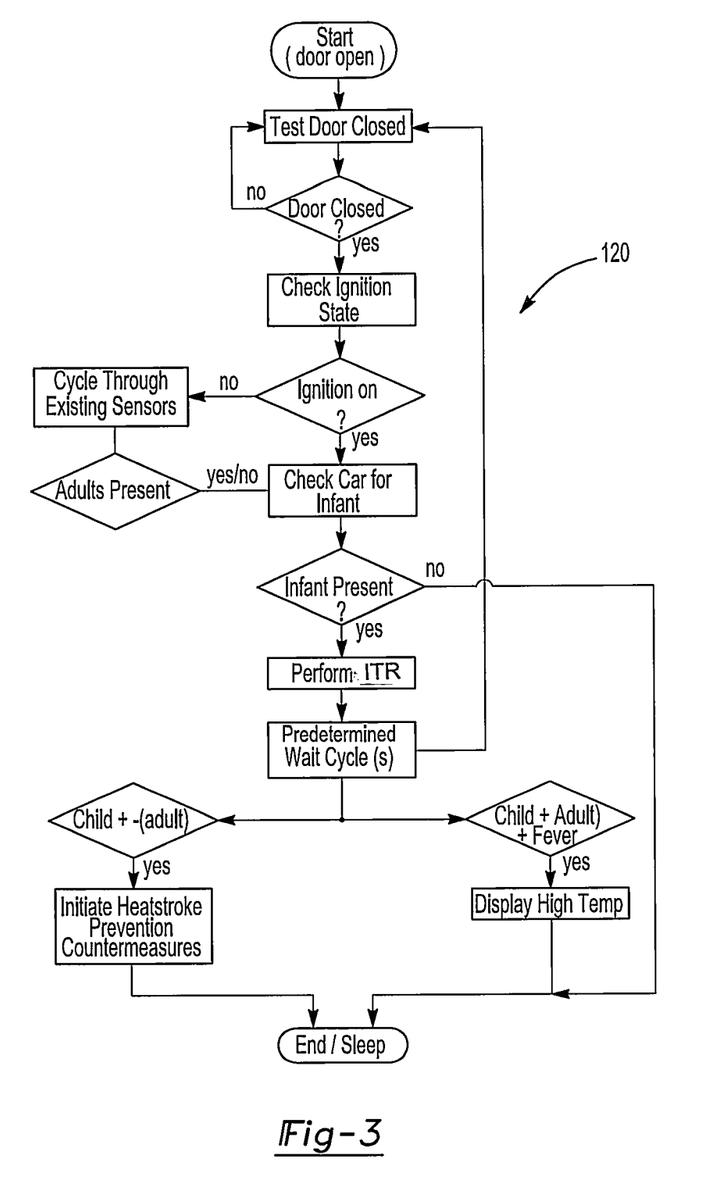
FIG. 3 depicts a flow chart according to one embodiment of the present specification according to one or more embodiments shown and described herein.
Figure 5:
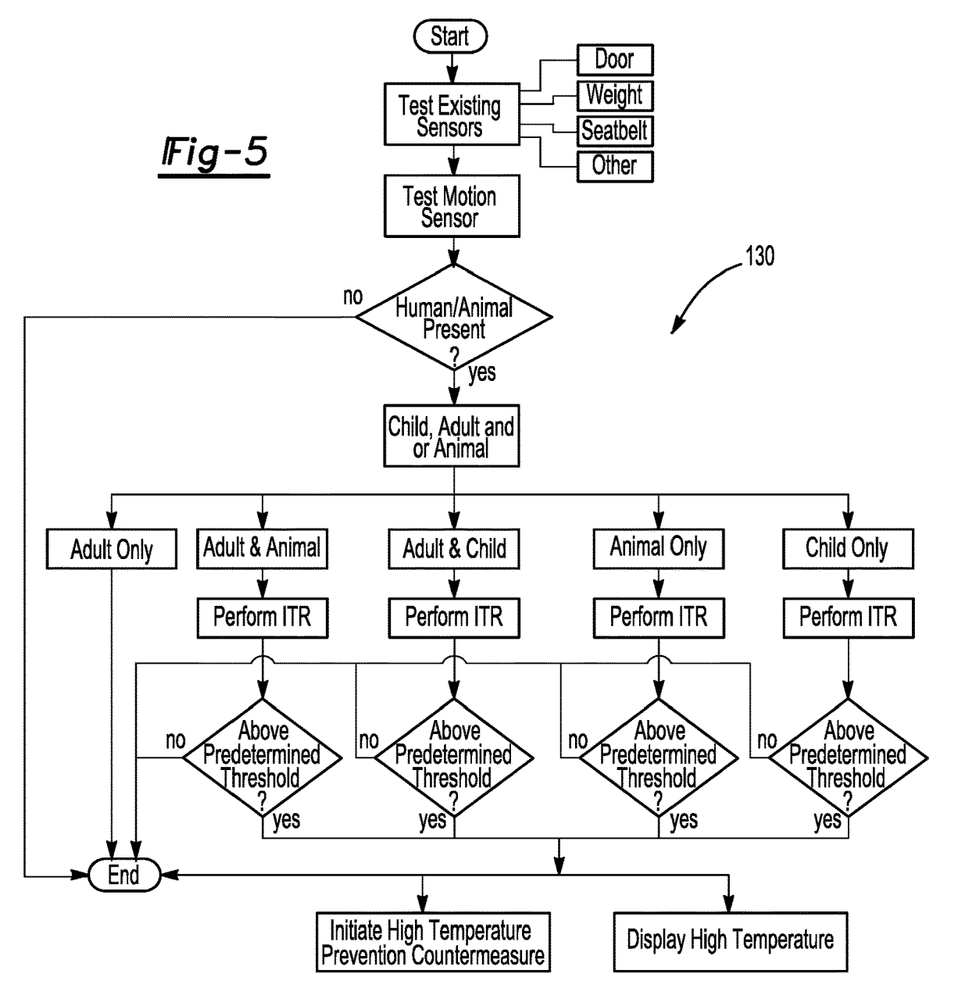
FIG. 5 depicts a flow chart according to another embodiment of the present specification according to one or more embodiments shown and described herein.
Figure 6:
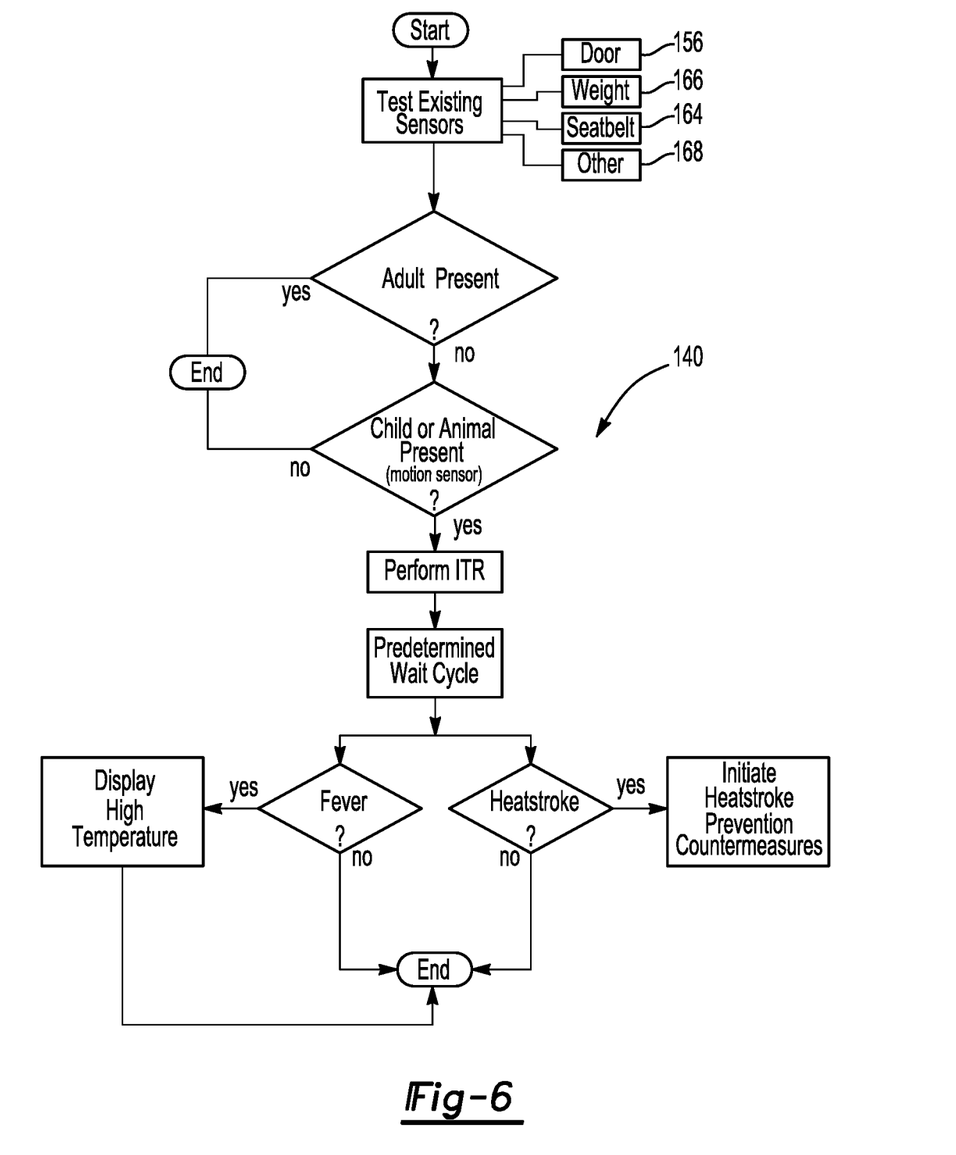
FIG. 6 depicts a flow chart according to yet another embodiment of the present specification according to one or more embodiments shown and described herein.
Figure 7:
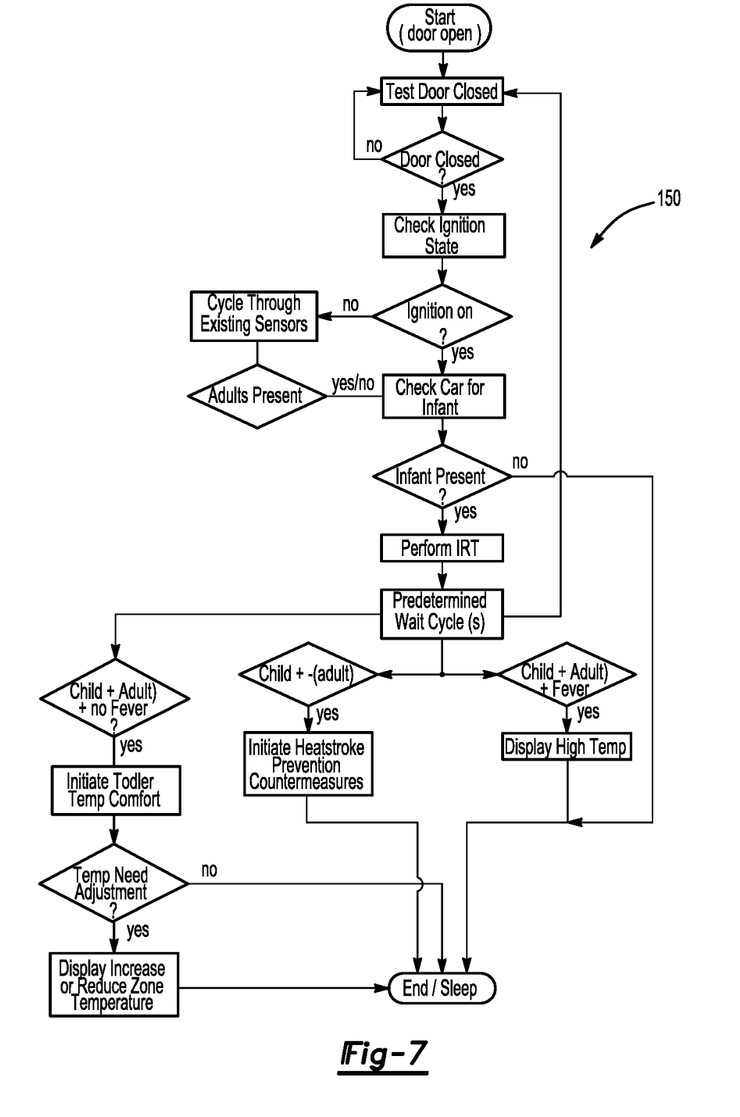
FIG. 7 depicts yet another embodiment of the system of the present specification according to one or more embodiments shown and described herein.

Description of Detection for Illness:

The operation of opening and closing the door(s) will activate the system. The chip will communicate with the vehicle processor 152 (i.e. the vehicle's central processing unit (CPU)) to verify the action. The ignition on status is then checked. If in the "on" position, the process for preventing checking for maladies such as but not limited to high fever will begin. Front passenger detection stage will begin by checking to see if seatbelts are unlatched. If latched, the system will proceed to the next step. Examples of this process are illustrated in the flowcharts as illustrated in FIGS. 3, 5 and 6.

Occupant sensor interrogation allows the system to use the existing vehicle sensors in the present system. For cars equipped with occupant sensors, such as those used to determine the weight of front passengers to determine airbag deployment velocity, will be checked for adult occupancy. If adult is present, the system will proceed to the next stage. Strategically placed IR cameras or equivalent will turn on and scan for the presence of a child seated in a car seat.

In some embodiments, signal processing will then deploy to process data from infrared camera or equivalent. If one is present, a temperature reading will be taken, and if a high fever, or other malady is detected, the driver, and or passenger will be warned through the vehicles warning systems. Examples of this process are illustrated in the flowcharts as illustrated in FIGS. 3, 5 and 6.

Description Heatstroke Detection and Prevention:

The operation of opening and closing the door will activate the system. Other triggers may also activate the system (i.e. such as a dramatic decrease in weight in the driver seat, seatbelt unfastening . . . etc.). The existing vehicle sensors will communicate with the processor (i.e. the vehicle's central processing unit (CPU)) to verify the action and initiate the processes as illustrated in the flowcharts as depicted in FIGS. 3, 5 and 6.

Once this first step of conditional probability is established, the ignition off status will be checked for being in the off position. If in the "off" position, the process for preventing heatstroke will start in accordance with the flowcharts as illustrated in FIGS. 3, 5 and 6.

Front passenger detection stage will begin by checking to see if seatbelts are unlatched. If unlatched, the system will proceed to the next step.

Occupant sensor interrogation. For cars equipped with occupant sensors, such as those used to detect weight for airbag deployment velocity, if they are off, an indication of the absence of an adult, the system will proceed to the next stage.

As with prior embodiments, strategically placed IR cameras or equivalent will turn on and scan for the presence of a child seated in a car seat. If one is present, an alarm or other type of warning will activate after a prescribed amount of time to avoid false activation caused by the delay between an adult exiting the vehicle, and getting around to the back of the vehicle to collect their child. If no response is detected, system will turn on the vehicle, and in turn, its air-conditioning system thus restoring cabin temperature to a safe level. It will do this while still maintaining applicable security settings.

EMBODIMENT EXAMPLE 1

In one embodiment, the processor takes the following described steps and actions. The action of the door opening and closing initiates the system. It would then wait for a predetermined amount of time to make sure that no other doors are going to open then close. Once that time period is over, it would interrogate the other sensors. If the ignition is in the ON position, then the system assumes that the car is running and assumes that there is an adult present. If at least one front seatbelt is in use, another indication that there is an adult present. Using a weight sensor to determine the presence of an adult: if the weight sensor determines that there is someone more than 75 pounds in the seat, this is further indication that there is an adult present. Other sensors such as eye monitors or facial recognition sensors, provide additional indication about the presence of an adult.

If an adult is determined to be in the vehicle, the vehicle will use the infrared sensor to see if a child is seated in the car seat by taking a picture. If the (CPU) processor does determine that an adult is present, then the system will end. The child's temperature reading is taken by the same infrared sensor (i.e. infrared camera). If elevated (indicating likely infection and/or illness), it is indicated within the vehicle warning system in the dashboard where the caregiver and/or driver is notified. Additionally, the child's breathing is constantly monitored by movement sensor (a radar sensor, as described above) for normal breathing. For example, if a child is choking, a warning is displayed in the vehicle warning system in the dashboard.

EMBODIMENT EXAMPLE 2

In other embodiments and variations, the action of the door opening and closing initiates the system. It would then wait for a predetermined amount of time to make sure that no other doors are going to open then close. Once that time period is over, it would interrogate the other sensors. If the ignition is in the OFF position, then the processor determines that an adult is absent. If the seatbelt is not engaged, then the processor has another indication that there is no adult present. Similarly, if the weight sensors is registering greater (less than) than 75 pounds, the processor then assumes that there is no adult present. Other sensors such as eye monitors or facial recognition sensors, provide additional indication about the presence of an adult.

If, based on these existing sensors, an adult is not determined to be in the vehicle then the vehicle will use the temperature sensor (i.e. infrared camera) to see if a child is seated in the car seat by taking a picture. If they are, the child's temperature reading is taken by the same infrared camera. If elevated/reduced (indicating likely heatstroke or hypothermia), then the vehicle will on AC or heater as instructed by the processor. It then sends a text or calls the caregiver to alert them of the situation. Option for the car alarm to turn on or remain off. User can turn this feature on or off.

If the child is not registering in the car seat, but movement sensor movement sensor (radar, as discussed above) is registering movement, likely infant or pet, the processor may still have the option to turn the AC on. If the ambient temperature is greater than a predetermined threshold, then the AC will turn on.

EMBODIMENT EXAMPLE 3

In yet another embodiment, the action of the door opening and closing initiates the system. It would then wait for a predetermined amount of time to make sure that no other doors are going to open then close. Once that time period is over, the processor will interrogate the other sensors. If the ignition is in the ON position, then the system assumes that the car is running and assumes that there is an adult present. If at least one front seatbelt is in use, another indication that there is an adult present. Using a weight sensor to determine the presence of an adult: if the weight sensor determines that there is someone more than 75 pounds in the seat, this is further indication that there is an adult present. Other sensors such as eye monitors or facial recognition sensors, provide additional indication about the presence of an adult. If all sensors are indicating that there is an adult absence, then the processor will use the temperature sensor (infrared camera) to capture an image. The vehicle will use the infrared sensor to see if a child is seated in the car seat by taking a picture. The child's temperature reading is taken by the same infrared camera. If elevated/reduced (indicating likely heatstroke or hypothermia), Vehicle turns on AC or heater. It then sends a text or calls the caregiver to alert them of the situation. Option for the car alarm to turn on or remain off. User can turn this feature on or off.

EMBODIMENT EXAMPLE 4

In yet another embodiment, the action of the door opening and closing initiates the system. The processor then waits for a predetermined amount of time to make sure that no other doors are going to open then close. Once that time period is over, it would interrogate the other sensors. In this embodiment, if the ignition is in the ON position, the processor assumes that the car is running and that an adult is present. The processor further assumes that if at least one front seatbelt is in use, another indication that there is an adult present. Furthermore, the system can look to the weight sensor where if the weight sensor is registering greater than 75 pounds, there is more indication that adult is present. Similarly, eye monitors can provide additional indication about the presence of an adult.

If an adult is determined to be in the vehicle, the vehicle will use the infrared sensor to see if a child is seated in the car seat by taking a picture. If they are, no need to worry about heat stroke at this point.

In one scenario, the child's temperature reading is taken by the same infrared camera. The system determines that toddler is not suffering from infection but is likely uncomfortable. The fact is indicated within the vehicle warning system in the dashboard where the caregiver is notified; and given the option to adjust temperature accordingly or the system can make automatic adjustments if care giver has that option engaged.

In another scenario, the child's breathing is constantly monitored by movement sensor (actually, small radar) for normal breathing. If a child is chocking for instance, that fact is displayed in the vehicle warning system in the dashboard.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A vehicle occupant temperature sensing system comprising:
   at least one existing sensor within a vehicle, the existing sensor being a door sensor to determine if a door has been opened or closed, activating the system only if the door sensor detects opening and subsequent closing of the door;
   a motion sensor provided within an interior of the vehicle, and a processor configured to determine if a child, adult or animal is contained within the vehicle;
   the processor configured to determine the presence of a child, adult or animal based on data received from an ignition sensor, a weight sensor and the motion sensor wherein:
      if the processor determines that an adult is present within the vehicle based on information from the ignition sensor, the weight sensor and the motion sensor, then the process ends;
      if the processor determines that a child or animal is within the vehicle, and no adult is within the vehicle, based on information from the an infrared camera and the motion sensor, then a temperature sensor takes the temperature of the child or animal within the vehicle;

wherein if it is determined that the temperature of the child or animal within the vehicle is above a predetermined threshold, then corrective actions are taken.

2. The vehicle occupant temperature sensing system of claim 1 wherein the temperature sensor is an infrared camera.

3. The vehicle occupant temperature sensing system of claim 1 wherein the door sensor sends a signal to the processor if it determines that a driver has left the vehicle, but the passengers may not have left the vehicle.

4. The vehicle occupant temperature sensing system of claim 1 wherein a facial recognition sensor is provided.

5. The vehicle occupant temperature sensing system of claim 1 wherein the processor is configured to control corrective actions of the vehicle if it is determined that the temperate of the child or animal is elevated.

6. The vehicle occupant temperature sensing system of claim 5 wherein the corrective action include turning on the air conditioning.

7. The vehicle occupant temperature sensing system of claim 1 where a display message is conveyed to a user of the vehicle if an elevated temperature is detected.

8. The vehicle occupant temperature sensing system of claim 7 where a display message is conveyed to the user if the elevated temperature may be associated with an illness.

9. A vehicle occupant temperature detection system comprising:
  at least one existing vehicle sensor, the existing sensor being a door sensor to determine if a door has been opened or closed, activating the system only if the door sensor detects opening and subsequent closing of the door;
  a temperature sensor configured to acquire a body temperature of a vehicle occupant, the temperature sensor activated only upon a signal from the door sensor that an occupant is in the vehicle; and
  a processor in communication with the temperature sensor, the processor configured to determine if the body temperature of the occupant is above or below a predetermined threshold;
    determining, based on information from an ignition sensor, a weight sensor, an infrared camera and the motion sensor if, an occupant within the vehicle as an adult or child, this process repeating for each occupant within the vehicle;
    if a child is within the vehicle based on information from the motion sensor and the infrared camera, then the temperature sensor takes the temperature of the child within the vehicle;
  wherein if both an adult and a child is determined to be in the vehicle and it is determined that the temperature of the child within the vehicle is above the predetermined threshold, then the processor is configured to notify a user of the elevated temperature or configured to take corrective measures to reduce the body temperature of the occupant.

10. The vehicle occupant temperature detection system of claim 9 wherein the corrective measure includes rolling down at least one window of the vehicle.

11. The vehicle occupant temperature detection system of claim 9 wherein the corrective measure includes adjusting vehicle temperature to make the child more comfortable.

12. The vehicle occupant temperature detection system of claim 9 wherein the corrective measure includes displaying the high body temperature on a display panel within the vehicle.

13. The vehicle occupant temperature detection system of claim 9 wherein the processor is configured to determine if the elevated temperature is affiliated with a fever, if the processor determines that the elevated temperature is affiliated with a fever, the temperature is displayed or a zone temperature is reduced.

14. The vehicle occupant temperature sensing system of claim 9 wherein the at least one existing sensor is a door sensor wherein a signal is sent to the processor if it determines that a door on the vehicle has been opened.

15. The vehicle occupant temperature sensing system of claim 9 wherein the at least one existing sensor is a facial recognition sensor.

16. The vehicle occupant temperature sensing system of claim 1 wherein the trigger to start the system is the vehicle door opening.

17. A method of determining temperature of an occupant within a vehicle, the method comprising the steps of:
  activating the system by opening and subsequent closing of a door, detection of opening and subsequent closing of said door detected by means of a door sensor;
  determining if an adult is in the vehicle by:
    checking the status of the ignition, if the ignition is on then cycling though sensors to determine if an adult is present in the vehicle, the sensors including seatbelt, weight and/or motion sensors to determine if an adult is present; and
  determining if a child or animal is in the vehicle by means of a motion sensor and infrared camera;
    if only a child or animal is determined to be in the vehicle, then the temperature of the child or animal is taken, if the temperature is above a predetermined threshold, then corrective measures are taken to adjust the temperature of the child or animal by turning on the HVAC to prevent heat stroke or hypothermia;
    if a child or animal and adult is present in the vehicle as verified by the motion sensor and the infrared camera, then the temperature of the child or animal is taken, if the temperature is above a predetermined threshold, then the temperature is displayed to the adult indicating a fever.

* * * * *